(12) United States Patent
Gallup et al.

(10) Patent No.: US 6,472,203 B1
(45) Date of Patent: Oct. 29, 2002

(54) COMBINATION AIR SAMPLING CASSETTE AND NUTRIENT MEDIA DISH

(75) Inventors: David Forrest Gallup, Escondido, CA (US); Robert James Bolender, Fremont, CA (US); James Purves, Edinborough (GB); Lon E. Bell, Altadena, CA (US)

(73) Assignee: Environmental Microbiology Laboratory, Inc., San Bruno, CA (US)

( * ) Notice: Subject to any disclaimer, the term of this patent is extended or adjusted under 35 U.S.C. 154(b) by 0 days.

(21) Appl. No.: 09/705,300

(22) Filed: Nov. 1, 2000

Related U.S. Application Data

(60) Provisional application No. 60/163,012, filed on Nov. 1, 1999.

(51) Int. Cl.$^7$ ................................................ C12M 1/26
(52) U.S. Cl. ............................. 435/309.1; 435/305.4; 73/28.05; 73/863.22
(58) Field of Search ...................... 435/305.1, 305.4, 435/309.1; 73/28.05, 863.21, 863.22

(56) References Cited

U.S. PATENT DOCUMENTS

| | | | | |
|---|---|---|---|---|
| 3,001,914 A | * | 9/1961 | Andersen | 435/288.3 |
| 3,922,905 A | * | 12/1975 | Roth | 73/28.04 |
| 4,038,057 A | * | 7/1977 | Roth | 55/465 |
| 6,240,768 B1 | * | 6/2001 | Lemonnier | 73/28.05 |

* cited by examiner

Primary Examiner—David A. Redding
(74) Attorney, Agent, or Firm—Larry D. Johnson; Craig M. Stainbrook; Johnson & Stainbrook, LLP

(57) ABSTRACT

A combination air sampling cassette and nutrient media dish having base, orifice plate, and nutrient media dish assembly for the collection of airborne particles. The orifice plate includes a plurality of holes that brings the nutrient media dish into fluid communication with the ambient air. A pump is connected to the air outlet in the base to pull air into the orifice plate through the holes, over the culture media, and out through the air outlet. As the air passes through the holes in the orifice plate it is accelerated and results in the selected impaction of particles in the culture media. A cover fits over the assembly to protect the culture media prior to and after sampling.

39 Claims, 6 Drawing Sheets

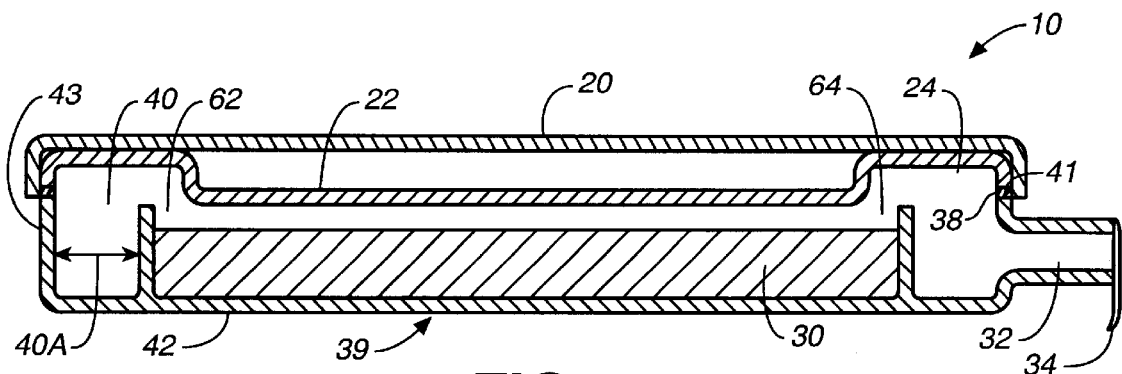
FIG._1
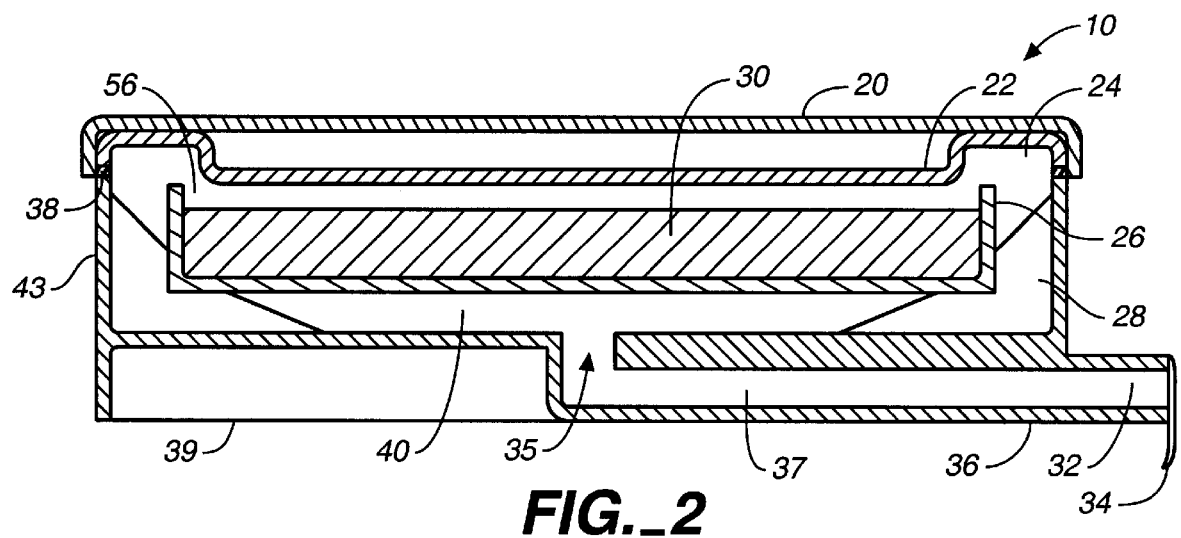
FIG._2
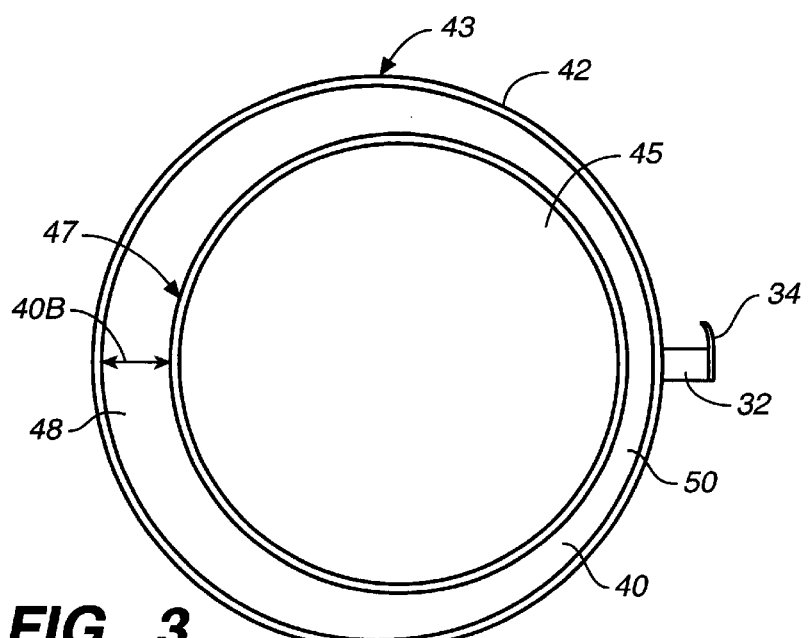
FIG._3

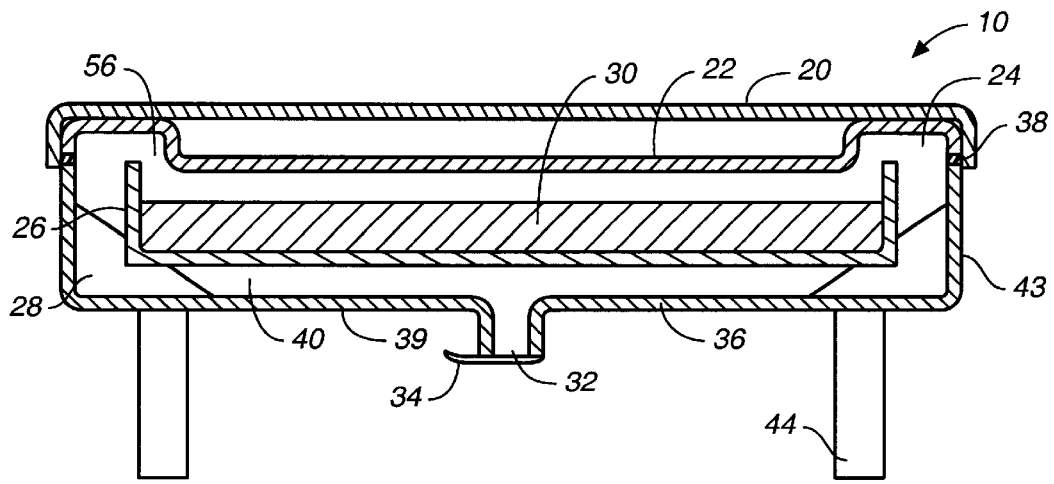
FIG._4
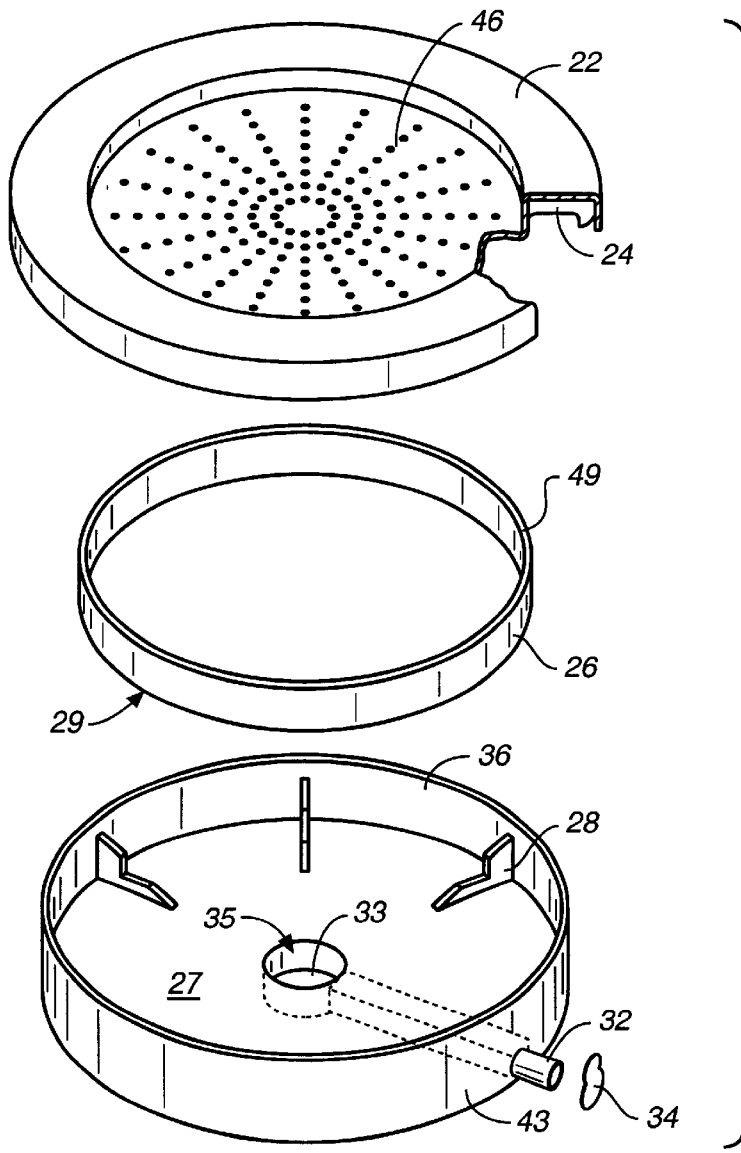
FIG._5

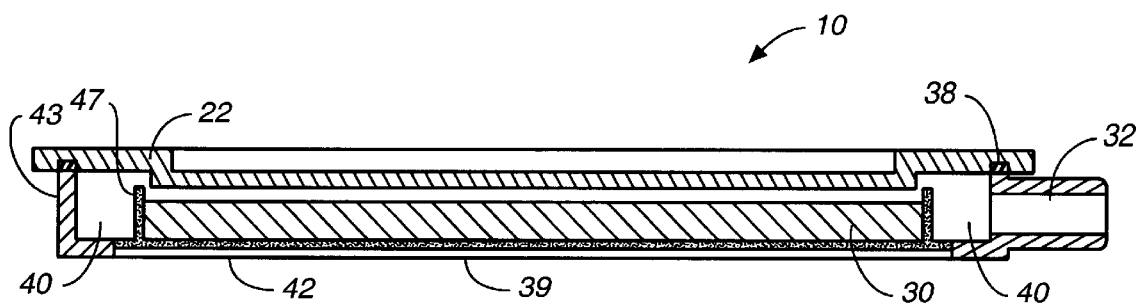
FIG._6
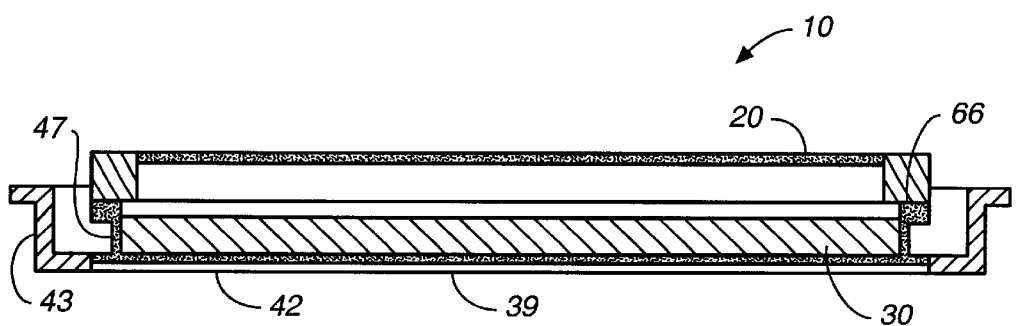
FIG._7
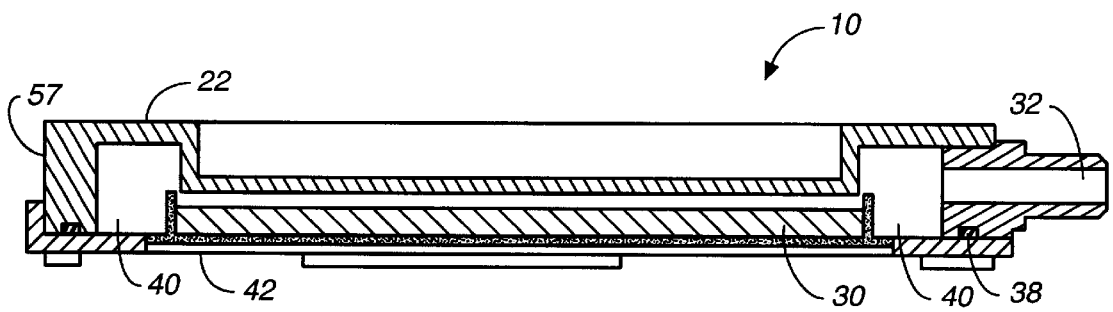
FIG._9
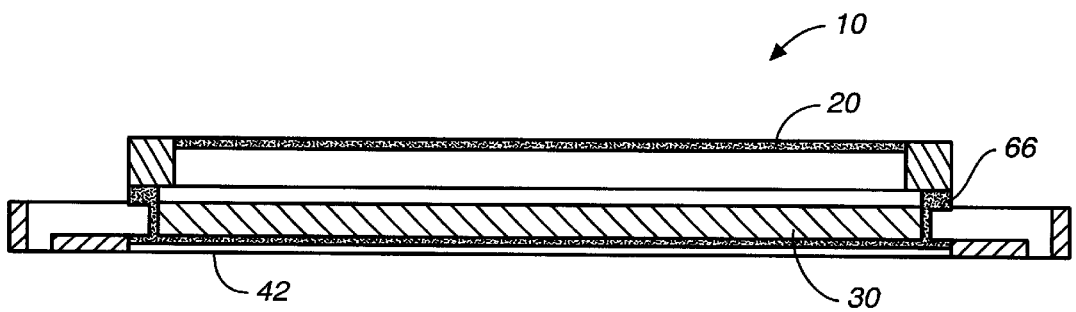
FIG._10

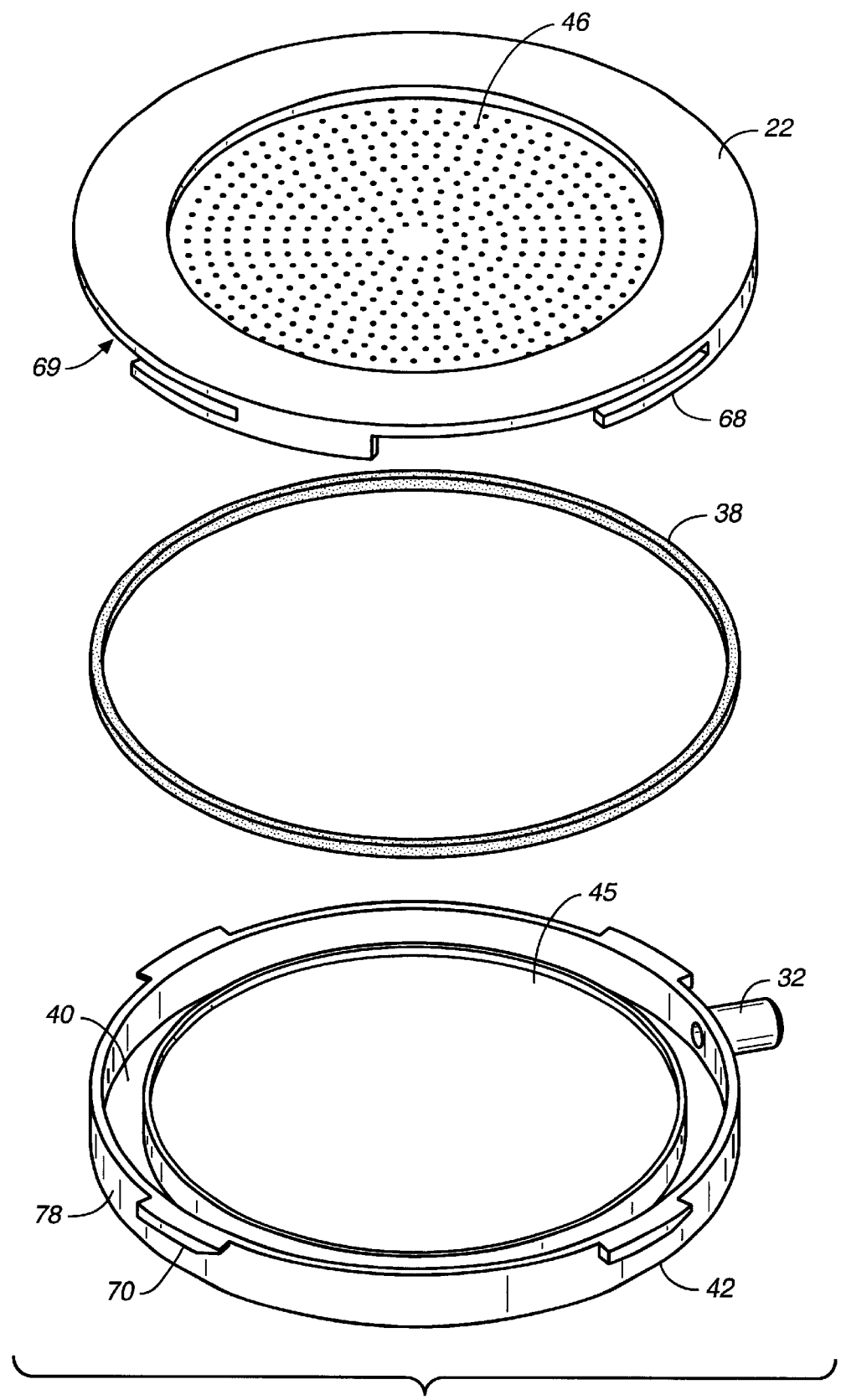
FIG._8

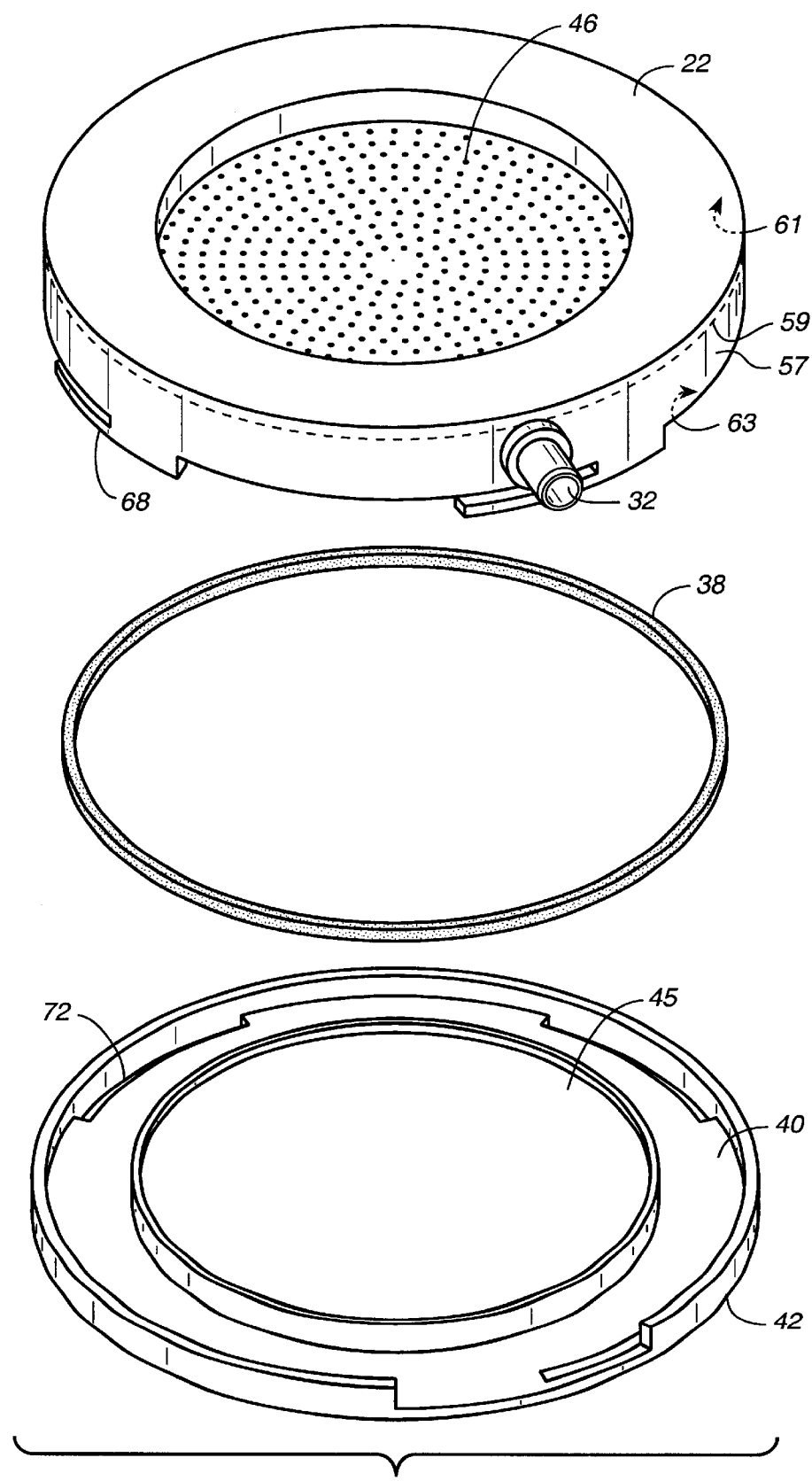
FIG._11

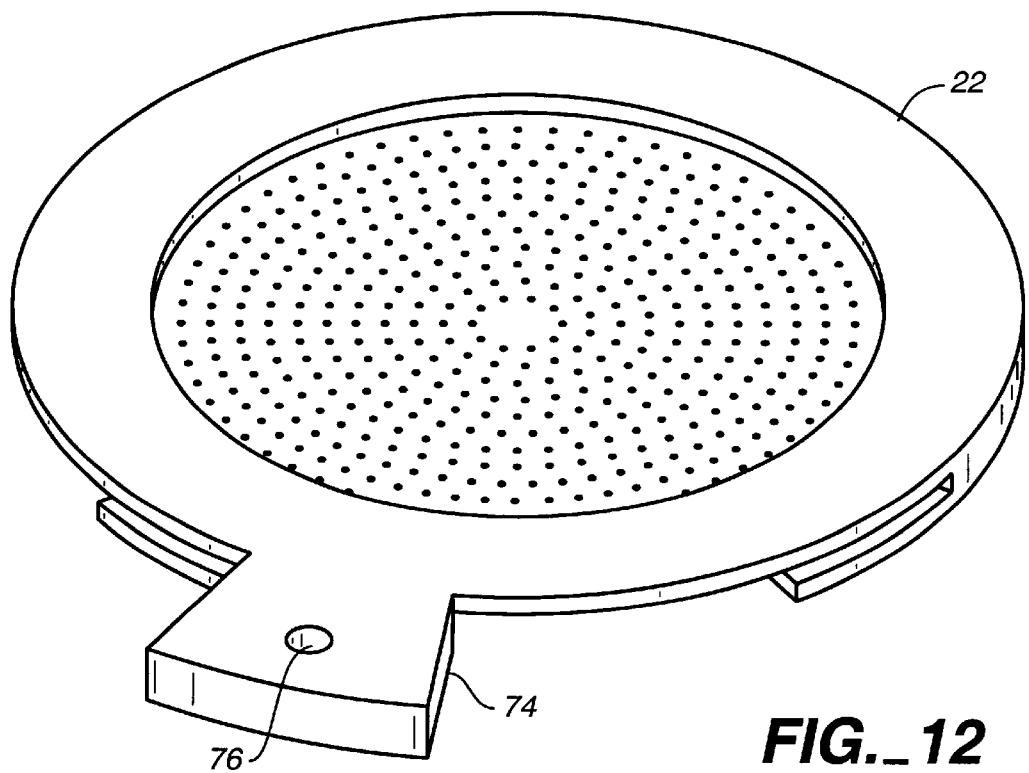
FIG._12
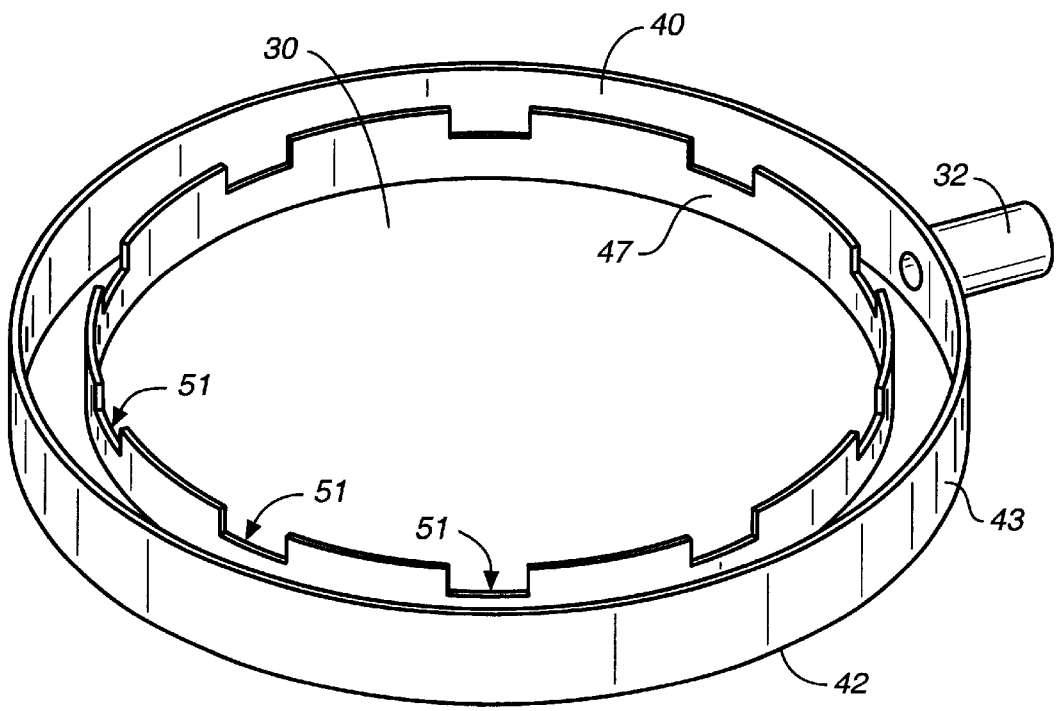
FIG._13

COMBINATION AIR SAMPLING CASSETTE AND NUTRIENT MEDIA DISH

CROSS REFERENCES TO RELATED APPLICATIONS

This application claims the benefit of the filing date of U.S. Provisional Patent Application, Serial No. 60/163,012, filed Nov. 1, 1999, and entitled, Culturable Cassette.

BACKGROUND OF THE INVENTION

1. Field of the Invention

This invention relates generally to an improvement in the field of culturable air sampling for biological materials, and more particularly to a combination air sampling cassette and nutrient media dish for the selective collection of viable microorganisms from ambient air for culturing and analysis.

2. Discussion of Related Art

The growing awareness of the potential adverse health effects of microorganisms has given rise to an increased need to detect and quantify airborne microorganisms during evaluation of indoor air quality. As is well-known, many respirable viable particulates are entrained in the air we routinely breathe. The prior art includes a number of ambient air samplers adapted for use in collecting such viable microorganisms. In operation, these devices generally enable the collection of viable microorganisms onto a culture media or nutrient to stimulate incubation and foster colony growth. Subsequent laboratory analysis will identify and enumerate the colonies.

A well-respected device in wide use in the field of viable sampling is the Andersen viable (microbial) sampler, disclosed in U.S. Pat. No. 3,001,914. The patent teaches a mechanism which serves to count and classify microorganisms in air. The device comprises a series of stages, each stage including a perforated member positioned over a layer of nutrient media. Airborne particles are impacted onto the nutrient when air is drawn through the device. On incubation the viable particles in the nutrient become visible as colonies. The device is available as a six-stage or two-stage system when particle sizing is required, or single-stage when particle sizing is not required.

The Andersen sampler has two fundamental disadvantages: it is expensive and it is inconvenient to use. Several commercially available devices have been developed to overcome the limitations of the Andersen sampler, including, for example, the RCS™ centrifugal air sampler, the PBI surface air system sampler (SAS), and the Mattson-Garvin Slit-to-Agar air sampler. (RCS is a registered trademark of Biotest AG Corporation, Federal Republic of Germany.) While these devices arguably provide greater ease of use, they are still expensive and, more significantly, do not exhibit the collection efficiency of the Andersen sampler [Reference:"Evaluation of Eight Bioaerosol Samplers Challenged with Aerosols of Free Bacteria", American Industrial Hygiene Association Journal (53), October 1992.]

Other devices similar to the Andersen design have been developed, including U.S. Pat. No. 3,922,905 and 4,038,057, both to Roth. The '057 patent teaches a sampling device for removing particulate matter from gaseous media by jet impaction. The sampler includes a base, and impaction stage, and a connector diffuser connected to the impaction stage. The impaction stage has a plate with apertures for generating a prescribed velocity of the gas as it passes through the apertures. A nutrient medium plate is positioned under the apertured plate and the gas passing through the apertures impacts the nutrient medium such that airborne particulates are captured. The Roth devices were intended to have lower equipment cost and be simpler to use, but they have not displaced the Andersen sampler as the device of choice, most probably because they are not, in fact, appreciably easier to use than the Andersen sampler.

Accordingly, there remains a need for a viable sampler that has demonstrable equivalence to the Andersen sampler in terms of performance but which has the advantages of ease of use and lower cost.

Objects and Advantages

Accordingly, the primary objects and advantages of the combination air sampling cassette and nutrient media dish of the present invention include:

1. to provide a viable sampler that has lower equipment cost;
2. to provide a viable sampler that is faster and easier to use; and
3. to provide a viable sampler that is smaller and lighter than currently known devices.

Further objects and advantages of the invention will become apparent from a consideration of the drawings and ensuing description.

SUMMARY OF THE INVENTION

The combination air sampling cassette and nutrient media dish of the present invention generally comprises a base and media dish assembly that defines an upwardly opening recess therein, an air outlet therefrom, and an enclosure retaining culture media for the collection of particles. In a first preferred embodiment, an orifice plate comprising a plate with a plurality of small holes fits onto the integrated media dish in a sealing arrangement. A pump is connected to the air outlet in the base to pull air through the orifice plate, over the culture media, and out through the air outlet. As the air passes through the holes in the orifice plate it is accelerated and results in the selected impaction of particles in the culture media. A cover fits over the assembly to protect the culture media prior to and after sampling.

BRIEF DESCRIPTION OF THE DRAWINGS

FIG. 1 is a cross-sectional side view in elevation of a first preferred embodiment of the combination air sampling cassette and nutrient media dish of the present invention, showing an ultra low profile configuration in which the orifice plate-media dish air passageway is substantially uniform in width;

FIG. 2 is a cross-sectional side view in elevation of a second preferred embodiment of the present invention, showing a low profile configuration of a combination air sampling cassette;

FIG. 3 is a top plan view of a variation of the inventive apparatus showing a variable width air passageway, said view showing the top cover and orifice plate removed;

FIG. 4 is a cross-sectional side view in elevation of a third preferred embodiment of the combination air sampling cassette and nutrient media dish of the present invention;

FIG. 5 is an exploded assembly perspective view of the low profile configuration of the cassette shown in FIG. 2, showing only the orifice plate, the media dish, the base, and the outlet seal;

FIG. 6 is a cross-sectional side view in elevation of a fourth preferred embodiment of the combination air sampling cassette and nutrient media dish of the present invention that utilizes a removable and reusable orifice plate with the air outlet contained in the combined base-media dish;

FIG. 7 is a cross-sectional side view in elevation of the cassette of FIG. 6 with the orifice plate removed and the cover in place;

FIG. 8 is an exploded isometric view of the cassette of FIG. 6;

FIG. 9 is a cross-sectional side view in elevation of a fifth preferred embodiment of the combination air sampling cassette and nutrient media dish of the present invention that utilizes a removable and reusable orifice plate with the air outlet contained in the orifice plate;

FIG. 10 is a cross-sectional side view in elevation of the air sampling cassette of FIG. 9 with the orifice plate removed and the cover in place;

FIG. 11 is an exploded isometric view of the cassette of FIG. 9; and

FIG. 12 is a perspective view of an orifice plate with a mounting flange and tapped hole.

FIG. 13 is a perspective view of a combination air sampling cassette and nutrient media dish with cut-outs in the media dish wall.

DETAILED DESCRIPTION OF THE PREFERRED EMBODIMENTS

FIGS. 1 though 11 depict several different embodiments of the combination air sampling cassette and nutrient media dish of the present invention, generally denominated 10 herein. FIGS. 1 through 5 depict embodiments where the orifice plate 22 remains in place as an integral part of the air sampling cassette. FIGS. 6 through 11 depict embodiments of the design where the orifice plate 22 is removable and re-usable.

FIG. 1 is a cross-sectional side view in elevation of a first and most fundamental embodiment of the combination air sampling cassette and nutrient media dish 10 of the present invention. This embodiment is an ultra low profile configuration, comprising a base 42, preferably substantially cylindrical and having a bottom 39, a contiguous side 43 (preferably circumferential), and an integral contiguous interior partition 47 substantially concentric with said side 43 and thereby defining an integral culture media dish portion 45. The cassette includes a removable cover 20, and an orifice plate 22 interposed between the base 42 and the cover when the cover is on. The upper edge 41 of base side 43 extends slightly higher than the upper edge 49 of the media dish partition 47, such that an air exit gap 62, 64 is defined by the orifice plate 22 and the upper edge 49 of the media dish 45. The cassette further includes an outlet port 32 having an outlet seal 34 that may be selectively opened and closed. The side 43 of the base 42 and the partition 47 of the media dish 45 are spaced apart, preferably substantially evenly, to define an air passageway 40 of substantially uniform width 40A and in fluid communication with the outlet port. Alternatively, as shown more clearly in FIG. 3, the width 40B of the air passageway may be varied to channel air in desirable circulation patterns to facilitate impaction of microorganisms onto the nutrient media and to provide for a uniform and balanced flow of air through the orifice plate. This variation is applicable to each of the preferred embodiments. Thus, FIG. 3 is generic to each of the embodiments. A perimeter seal 38 between orifice plate 22 and the upper edge 41 of the side 43 prevents the introduction of atmospheric gases from entering the interior of the cassette without passing through the specifically sized apertures of the orifice plate.

In operation, a nutrient medium 30 is introduced into the media dish 42 and the cover is removed. A suction pump (not shown) is connected to the outlet port 32 to draw air through the orifices (see FIG. 5), and viable organisms and other particulate impact on the surface of the nutrient medium. The air then moves outwardly from the dish through air exit gap 56 and into air passageway 40 for ultimate exhausting through outlet port 32. Both the exit gap and the air passageway may be varied in width. Also, the height of the media dish partition 47 may be varied over its length and may include a plurality of discrete cut-outs in the media dish partition 47 that may vary in size and distribution over its length, as shown in FIG. 13.

FIG. 2 is a cross-sectional side view in elevation of a second preferred embodiment of the present invention, showing a low profile configuration of a air sampling cassette; and FIG. 5 is an exploded assembly perspective view thereof, showing the low profile configuration without a cover. In this embodiment, the air outlet port 32 opens at substantially the center 33 of base 36 and directly underneath the bottom 29 of the media dish 26, which is supported above the interior bottom surface 27 of base 36 by media dish locating or support ribs 28. From outlet port opening 35 an outlet duct extends to the discharge opening 32 for exhausting air. This configuration allows the media dish 26 to be removably placed within the base 36 and for air to flow substantially symmetrically around and underneath the media dish 26, and then to exit from the side of the base 36 through the outlet port 32.

FIG. 4 is a cross-sectional side view in elevation of a third preferred embodiment of the combination air sampling cassette and nutrient media dish of the present invention. This view shows a variation on the design of FIGS. 2 and 5, in which the outlet port 32 is underneath the base 36, preferably though not necessarily at substantially the center of the base, and wherein base legs 44 elevate the base from the surface on which it is placed so that a pump connection can be made to the outlet port 32. The advantage of this configuration is that it has a low tooling cost when the base 36 is molded.

FIG. 6 is a cross-sectional side view in elevation of a fourth preferred embodiment of the combination air sampling cassette and nutrient media dish of the present invention; FIG. 7 is a cross-sectional side view in elevation of the air sampling cassette of FIG. 6 with the orifice plate removed and the cover in place; and FIG. 8 is an exploded isometric view of the air sampling cassette of FIGS. 6 and 7. This embodiment utilizes a removable and reusable orifice plate 22 with the air outlet 32 integral with the combination base-media dish 42. The orifice plate 22 includes a bayonet mounting means comprising a plurality of spaced-apart integral tangs 68 disposed downwardly from the underside 69 of the orifice plate and adapted for rotatable mating with complementary flanges 70 integral with the exterior circumference 78 of said base member 42. As with the first preferred embodiment, shown in FIGS. 1 and 3, the media dish portion 45 is integral with the base and defined by a partition 47 interior to the side 43 of base 42.

FIG. 9 is a cross-sectional side view in elevation of a fifth preferred embodiment of the combination air sampling cassette and nutrient media dish of the present invention. This design is a variation on the fourth preferred embodiment and also utilizes a removable and reusable orifice plate 22. The distinction is that the air outlet 32 is integral with a contiguous circumferential side 57 of the orifice plate, rather than with the side of the base, and further that the bayonet mounting means involves the use of a plurality of interior slots 72 defining interior flanges integral with the base and adapted for mating with tangs 68 integral with the orifice plate 22. FIG. 10 is a cross-sectional side view in elevation of the air sampling cassette of FIG. 9 with the orifice plate removed and the cover in place, and FIG. 11 is an exploded isometric view of the air sampling cassette of FIG. 9. Each of the fourth and fifth embodiments involves the use of a gasket 38, or O-ring, but may also employ any another method, to provide a secure seal between the orifice plate and base member.

As may be readily appreciated, the side 43 (FIGS. 1–7, 13), 78 (FIG. 8), and 57 (FIG. 11) of the cassette may either be integral with the base or integral with the orifice plate, and this variation determines the structure that defines the air passageway and the structure from which the air outlet port extends. When the side is integral with the orifice plate, as in FIG. 11, the upper edge 59 of the side is defined by the interior intersection of the interior top portion 61 of the orifice plate and the interior side 63 of side 57. Whether the side is integral with the orifice plate or the base does not affect the principle of operation, and in either case the inventive combination obtains.

FIG. 12 is a perspective view of an orifice plate with a mounting flange 74 and a tapped hole 76.

There are several advantages in having the media dish integral with the cassette base, as illustrated in FIGS. 1, 3, and 6 through 11. This allows for an extremely low profile design. At the preferred flow rate of 28.3 liters per minute the flow will be symmetrical as the air exits out of the integral media dish 45 and into the air passageway 40 before leaving through the outlet port 32. However, at flow rates other than the preferred, the flow as the air exits the integral media dish 45 may not be symmetric. In these cases symmetry might be achieved by adjusting the width of the air passageway 40 as shown in FIG. 3. In FIG. 3, the air passageway 40 varies in width as shown by the wide air passageway 48 and the narrow air passageway 50. Another means of achieving a symmetrical flow would be to adjust the orifice plate-media dish air exit gap 56, as can be seen in FIG. 1. In FIG. 1, there is a large orifice plate-media dish air gap 62 on one side that is reduced to a small orifice plate-media dish air gap 64 on the opposite side. This change in gap size may be achieved by adjusting the design of the orifice plate 22 and or the media dish 45 (the media dish portion 45 is an integral part of the base 36 in this design configuration). Another means of achieving a symmetrical flow would be to vary the height of the media dish partition 47, which may further include a plurality of discrete cut-outs 51 in the media dish partition 47 that may vary in size and distribution over its length, as shown in FIG. 13. This feature is suitable for incorporation into any of the preferred embodiments of the inventive combination air sampling cassette and nutrient media dish.

The alternative embodiments provide for a removable media dish 26, as illustrated in FIGS. 2, 4, and 5. A parameter of the base 36 in these embodiments is how the media dish 26 attaches and locates relative to the base 36. Possible design configurations for this include, but are not limited to, the following:

1. Using locating ribs on the base 36 to locate the media dish 26 and using any method to hold it in place (solvent bonding, press fit, ultrasonic welding, spin welding, glue, snap into place, etc.).
2. Using ribs on the media dish 26 to center it within the base 36 and using any method of holding it in place (solvent bonding, press fit, ultrasonic welding, spin welding, glue, snap into place, etc.)

Culture media 30 is held in the media dish 26 or combined base-media dish 42. Air impinges upon the media 30 during sampling. Viable organisms will then germinate and grow upon the media 30 for identification after sampling. It is important that the bottom of the media dish 26 is rigid so that it does not flex while the sample is being taken.

As is evident in the design variations of the above-described first through fourth embodiments of the present invention, possible variations of the media dish 26 would include, but are not limited to, the following:

1. Having stiffening ribs on the bottom (top side of the bottom or the bottom side of the bottom);
2. Having a post in the center of the plate, on the top surface, to support the bottom of the orifice plate 22;
3. Having the media dish 26 be an integral part of the base 36 (with or without the stiffening ribs or a center post);

The function of the orifice plate 22 is to accelerate and concentrate the air flow into discrete, countable, sections. It has a plurality of evenly spaced apertures (typically 200 to 400, with 400 being preferred) each having a small diameter, typically between 0.0100" and 0.0465" with 0.0100" being preferred. The key to this part is the consistent diameter of the holes in the plate. The holes should be spaced roughly evenly from each other. In embodiments of the design where the orifice plate 22 is not removable and reusable it would be desirable, although not critical, that this part be transparent. Transparency aids in the analysis of the sampled part and in determining if a sample has been taken.

Several well-known means of manufacturing this part include, but are not limited to, the following:

1. Injection molding the holes into a unitary plastic part.
2. Stamping the holes into a piece of metal and insert molding the piece of metal into a piece of plastic.
3. Laser cutting the holes into a plastic, injection molded piece.
4. Drilling the holes into a plastic, injection molded piece.
5. Drilling the holes in a piece of metal and insert molding this into a piece of plastic.
6. Etching the holes into plastic.
7. Etching the holes into a piece of metal and insert molding this into a piece of plastic.
8. Machining the part from a solid block of metal and drilling the holes.

Another important function of the orifice plate 22 is to control the distance between the apertured surface of the orifice plate 46 and the media 30. The design should be such that this distance is well controlled, will not vary due to manufacturing tolerances, and will not vary while the sampling is taking place. Consequently, the orifice plate 22 should not flex, nor should any of the supporting surfaces that hold it over the media 30. Factors affecting this include the thickness of any walls or surfaces that are involved, including the plate with the holes, the use of stiffening ribs to minimize any flexure, and minimizing the distance and number of bends in getting from the holes to where the orifice plate 22 is supported.

The designs shown in the FIGS. 2, 4 and 5, locate and keep the orifice plate 22 centered relative to the base 36 and to the media dish 26, 45 by using orifice plate locating ribs 24. These ribs have lead-ins towards the outside that aid in placing the orifice plate 22 onto the assembly. Features of this configuration include:

1. The ribs 28 also hold the orifice plate 22 off of the media dish 26 a controlled amount, thus providing a high degree of control over the gap between the outlet of the holes in the orifice plate 22 and the top surface of the media 30. The outer edge of the rim comes close to, but does not directly connect with the base 36 because that would reduce the amount of control over the gap between the outlet of the holes in the orifice plate 22 and the top surface of the media 30. A seal is provided over the resulting gap between the orifice plate 22 and the base 36 by the perimeter seal 38.

2. The outer edge of the orifice plate rim directly connects with the outer edge of the base 36. This provides for a secondary seal in case the perimeter seal 38 were to fail.

3. Try to have both the outer edge of the orifice plate rim connect with the outer edge of the base 36 and have the orifice plate locating rib 24 connect with the edge of the media dish 26. A means of facilitating this and allowing for manufacturing tolerances would be to have the orifice plate locating ribs 24 and or the media dish locating ribs 28 crush slightly, by design, and provide a snug fit.

4. Have the orifice plate locating ribs center and locate the orifice plate 22 relative to the media dish 26. The bottom of the outer rim of the orifice plate 22 would engage with a gasket that also engages with the base 36. This allows for larger manufacturing tolerances and controls the gap between the orifice plate 22 and the media 30.

The function of the perimeter seal 38 is to prevent air from entering the cassette by any route other than through the orifice plate holes 46 and further provide attachment of the orifice plate 22 to the base 36 or combined base-media dish 42. In the embodiments with a removable and reusable orifice plate 22, the perimeter seal 38 is preferably a toroidal gasket or O-ring. FIGS. 8 and 11 show an O-ring that is retained within the orifice plate 22. An alternative design would have a gasket applied to the combined base-media dish 42. In such a case the method of attachment and of maintaining compression of the o-ring or gasket is by a twist-on connection. FIG. 8 shows a tang 68 on the orifice plate 22 that engages onto a flange 70 on the combined base-media dish 26. FIG. 11 shows a tang 68 on the orifice plate 22 that engages into a slot 72 in the combined base-media dish 42. Other attachment means including, without limitation, spring clamps, bolts and quick release nuts, and a hinging mechanism disposed at one end and an over-center clamp directly opposite.

Possible design configurations for embodiments with an integral orifice plate 22 include, among others, a piece of tape going around the perimeter of the assembly (around the joint that is formed between the outer edge of the rim of the orifice plate 22 and the upper, outer edge of the base 36); a snap together assembly with a small gasket to provide a seal; a bead of glue that has been applied on the joint; an ultrasonic weld; and a solvent bond.

Additionally, certain design configurations can show evidence of tampering with the sampling device. A piece of tape that has been torn, for example, would indicate that the cassette might have been opened.

In embodiments of the invention where the orifice plate 22 remains in place as an integral part of the air sampling cassette (FIGS. 1 through 5) the cover 20 and outlet seal 34 function to prevent air from getting into the cassette when it is not desirable to do so.

The cover 20 may be a very simple and low cost part. Possible design variants include, tape over the opening, a plastic cover that just rests on top of the rest of the assembly or is taped or otherwise held in place, a snap-on lid, a piece of parafilm, a sheet of plastic wrap, such as SARAN WRAP.

The outlet seal 34 is a very simple and low cost part. Possible design variants include, but are not limited to, tape, a plug that pushes into, over, or onto the outlet port 32 (as shown in FIG. 7), a snap-on piece that covers the outlet port 32, a piece of Parafilm, and plastic wrap.

In embodiments of the invention where the orifice plate 22 is removable and reusable (FIGS. 6 through 11) the cover 20 has an integral cover seal 66 to prevent air from getting into the cassette when it is not desirable to do so. As shown in FIGS. 8 and 11, this is a gasket or O-ring. However, other design variants for the cover seal 66 include, without limitation, tape applied to a flange or other surface on the cover 20 and extending over a coplanar surface on the combined base-media dish 42; a piece of Parafilm; either of the foregoing methods applied to sealing on the outside wall of the combined base-media dish 42 in FIG. 8 and having an additional outlet seal 34 as described above; and any of the foregoing methods applied to sealing on the side 43 of the combined base-media dish 42 in FIG. 8 and having the outlet seal 34 sealed by a gasket from the inside and the gasket being affixed to the cover 20. In embodiments of the design where the air outlet port 32 exits the base side 43, an alternative design would be to recess the outlet port 32 into the base such that the outlet port 32 is below flush with the base side 43.

A further embodiment of the invention would be a combined base-media dish 42 with an attached cover 20.

FIG. 12 shows a orifice plate 22 with a mounting flange 74 and tapped hole 76. These features are to enable the attachment of the orifice plate to a standard camera tripod stand by way of either screwing it directly to the stand or by the attachment of a quick disconnect mechanism. Another option for the mounting of the device to a tripod stand would be the provision of a cup being screwed to the tripod stand into which the assembled device would locate.

Operation of Invention

The overall purpose of the invention is to allow the user to take a culturable sample of the air. The procedure is different depending on whether the version of the device has a removable and reusable orifice plate 22 or not. For a device with an integral orifice plate 22 that remains in place the operation is as follows:

1. Cover 20 and outlet seal 34 are removed.
2. A pump is connected to the air outlet port 32 of the cassette.
3. The pump is turned on.
4. The pump is turned off and the time over which the sample was taken is recorded.
5. The cover 20 and outlet seal 34 are replaced.

For a device with a removable and reusable orifice plate 22 the operation is as follows:

1. Cover 20 (and outlet seal 34, if applicable) is removed.
2. Orifice plate 22 is attached to the combined base-media dish 42.
3. A pump is connected to the air outlet port 32.
4. The pump is turned on.
5. The pump is turned off and the time over which the sample was taken is recorded.
6. Orifice plate 22 is removed.
7. Cover 20 (and outlet seal 34, if applicable) is replaced.

In addition to knowing the amount of time that the pump was on, it is also important to know the flow rate of the air that was passing through the cassette while the sample was being taken. This flow rate is normally approximately 28.3 liters per minute.

As may be readily appreciated, the combination air sampling cassette and nutrient media dish of the present invention is a low cost, easy-to-use product that offers several advantages over the existing devices: It has lower equipment costs; it is lighter; it is smaller; and it is faster to use. The embodiments of the present invention having an integral orifice plate also have the advantages that they virtually eliminate the possibility for cross contamination between samples. It thus eliminates the need to clean any specialized equipment between samples.

While this invention has been described in connection with preferred embodiments thereof, it is obvious that modifications and changes therein may be made by those skilled in the art to which it pertains without departing from the spirit and scope of the invention. Accordingly, the scope of this invention is to be limited only by the appended claims.

What is claimed as invention is:

1. A combination air sampling cassette and nutrient media plate for the collection of viable microorganisms from ambient air, said apparatus comprising:
   a base member having a bottom and a base member side with an upper edge;
   an interior partition having an upper edge extending slightly lower than said upper edge of said base member side, said partition integral with said base member and spaced apart from said base member side so as to define an integral culture media dish portion and an air passageway between said interior partition and said base member side;
   a removable cover for placement over said cassette and constructed so as to prevent air from entering into the cassette;
   a selectively removable orifice plate having an underside and a plurality of apertures, wherein said underside of said orifice plate is positioned on said upper edge of said base member side so as to define an air exit gap between said underside of said orifice plate, said base member side, and said interior partition upper edge, placing said culture media dish portion in fluid communication with said air passageway, wherein the apertures of said orifice plate place said culture media dish and the ambient air into fluid communication, and wherein said orifice plate is interposed between said base and said cover when said orifice plate is not removed from said base when said cover is placed over said cassette; and
   an air outlet port, said outlet port in fluid communication with said air passageway and adapted for connection to a suction pump.

2. The combination air sampling cassette and nutrient media plate of claim 1, wherein said base member side is integral with said base member.

3. The combination air sampling cassette and nutrient media plate of claim 2, further including a seal between said orifice plate and said base member.

4. The combination air sampling cassette and nutrient media plate of claim 1, further including coupling means for connecting said orifice plate to said base member side.

5. The combination air sampling cassette and nutrient media plate of claim 4, wherein said coupling means comprises a bayonet mounting system.

6. The combination air sampling cassette and nutrient media plate of claim 5, wherein said bayonet mounting system comprises a plurality of tangs integral with said orifice plate and a plurality of flanges integral with said base member side, said flanges and tangs adapted for complementary rotatable and removable mating.

7. The combination air sampling cassette and nutrient media plate of claim 6, wherein said flanges are disposed on an exterior surface of said base member side and said tangs are disposed on said underside of said orifice plate.

8. The combination air sampling cassette and nutrient media plate of claim 4, further including a gasket interposed between said orifice plate and said base member.

9. The combination air sampling cassette and nutrient media plate of claim 1, wherein said orifice plate has an integral side.

10. The combination air sampling cassette and nutrient media plate of claim 9, wherein said coupling means comprises a bayonet mounting system.

11. The combination air sampling cassette and nutrient media plate of claim 10, wherein said bayonet mounting system comprises a plurality of tangs integral with said side of said orifice plate, said tangs adapted for rotatable, removable mating with a plurality of flanges integral with said base member side.

12. The combination air sampling cassette and nutrient media plate of claim 10, further including a gasket interposed between said orifice and said base.

13. The combination air sampling cassette and nutrient media plate of claim 1, wherein said air passageway has a substantially uniform width.

14. The combination air sampling cassette and nutrient media plate of claim 1, wherein said air passageway has a variable width.

15. The combination air sampling cassette and nutrient media plate of claim 1, wherein said base member is substantially cylindrical.

16. The combination air sampling cassette and nutrient media plate of claim 1, wherein said outlet port includes a seal that may be selectively opened and closed.

17. The combination air sampling cassette and nutrient media plate of claim 1 wherein said outlet port is disposed outwardly from said base member side.

18. The combination air sampling cassette and nutrient media plate of claim 1, wherein said interior partition includes at least one cutout.

19. A combination air sampling cassette and nutrient media plate for the collection of viable microorganisms from ambient air, said apparatus comprising:
   a base member having a bottom with a center, an interior bottom surface, and a contiguous side with an upper edge;
   support means for locating and supporting a nutrient media dish above said interior bottom surface;
   a removable nutrient media dish having a bottom, said nutrient media dish positioned by said support means and having a circumferential side with an upper edge, wherein said circumferential side, said contiguous side of said base member, said dish bottom, and said interior surface of said base member are each spaced apart so as to define an air passageway;
   an orifice plate having an underside and a plurality of apertures, said orifice plate in sealing arrangement with said contiguous side of said base member, said orifice plate underside positioned on said upper edge of said contiguous side of said base member, and configured such that said orifice plate, said base member side, and said circumferential side of said removable culture media dish define an air exit gap, which places said culture media dish in fluid communication with said air passageway, wherein the apertures of said orifice plate place said culture media dish and the ambient air into fluid communication;
   an air outlet port integral with said base, said outlet port in fluid communication with said air passageway and adapted for connection to a suction pump; and a removable cover for placement over said cassette and constructed so as to prevent air from entering into the cassette.

20. The combination air sampling cassette and nutrient media dish of claim 19 wherein said support means comprises a plurality of spaced-apart ribs disposed around the interior of said contiguous side of said base member.

21. The combination air sampling cassette and nutrient media dish of claim 19 wherein said upper edge of said side of said nutrient media dish extends below said upper edge of said contiguous side of said base member.

22. The combination air sampling cassette and nutrient media dish of claim 19 wherein said base member is substantially cylindrical.

23. The combination air sampling cassette and nutrient media dish of claim 22 wherein said side of said nutrient media dish is substantially concentric with said side of said base.

24. The combination air sampling cassette and nutrient media dish of claim 22 wherein said side of said nutrient media dish is not concentric with said contiguous side of said base member, and wherein said air passageway has a variable width.

25. The combination air sampling cassette and nutrient media dish of claim 19, wherein said outlet port extends outwardly from said contiguous side of said base member.

26. The combination air sampling cassette and nutrient media dish of claim 25, wherein said base member includes a center in its interior bottom surface and further includes an outlet opening through said center, and an outlet duct such that said outlet opening and said outlet port are in fluid communication.

27. The combination air sampling cassette and nutrient media dish of claim 19 wherein said air outlet port extends downwardly from substantially the center of said base member.

28. The combination air sampling cassette and nutrient media dish of claim 27 having base legs to support said base member above the surface on which it is placed.

29. The combination air sampling cassette and nutrient media dish of claim 19 wherein said circumferential side of said nutrient media dish includes at least one cut out.

30. The combination air sampling cassette and nutrient media dish of claim 19, further including coupling means for connecting said orifice plate to said contiguous side of said base member.

31. The combination air sampling cassette and nutrient media dish of claim 30, wherein said coupling means comprises a bayonet mounting system.

32. A combination air sampling cassette and nutrient media dish, comprising:

a base member having a bottom;

an outer side;

an interior partition having an upper edge, said partition integral with said base member and spaced apart from said outer side so as to define an integral culture media dish portion and an air passageway between said interior partition and said outer side;

a removable cover for placement over said cassette;

an orifice plate for removable coupling with said base member, said orifice plate having an underside, an integral side extending above said upper edge of said internal partition when said orifice plate is coupled with said base member, and a plurality of apertures, and coupling means for coupling said orifice plate to said base member, wherein when said orifice plate is coupled to said base member, said orifice plate is interposed between base member and said cover when said cover is on, and said underside of said orifice plate and said internal partition define an air exit gap, thereby placing said culture media dish portion in fluid communication with said air passageway, wherein said plurality of apertures of said orifice plate place said culture media dish and the ambient air into fluid communication; and an air outlet port in fluid communication with said air passageway and adapted for connection to a suction pump; wherein said outlet port is disposed outwardly form said orifice plate side.

33. The combination air sampling cassette and nutrient media dish of claim 32, wherein said outer side is integral with said base member.

34. The combination air sampling cassette and nutrient media dish of claim 32, wherein said outer side is integral with said orifice plate.

35. The combination air sampling cassette and nutrient media plate of claim 32, further including a seal between said orifice plate and said base member.

36. The combination air sampling cassette and nutrient media plate of claim 32, wherein said coupling means comprises a bayonet mounting system.

37. The combination air sampling cassette and nutrient media plate of claim 36, wherein said bayonet mounting system comprises a plurality of tangs integral with said orifice plate side and a plurality of interior slots defining interior integral with said base member, said flanges and tangs adapted for complementary rotatable and removable mating.

38. The combination air sampling cassette and nutrient media plate of claim 32, wherein said outlet port includes a seal that may be selectively opened and closed.

39. A combination air sampling cassette and nutrient media plate, comprising:

a base member having a bottom and a base member side with an upper edge;

an interior partition having an upper edge, said partition integral with said base member and spaced apart from said base member side so as to define an integral culture media dish portion and an air passageway between said interior partition and said base member side;

a selectively removable orifice plate having an integral side, and underside, and a plurality of apertures, said orifice plate adapted for connection to said base member side such that said base member side and said orifice plate side combine to have a height greater than the height of the upper edge of said interior partition, wherein said underside of said orifice plate and said upper edge of said interior partition define an air exit gap between said underside of said orifice plate and said interior partition upper edge, thus placing said culture media dish portion in fluid communication with said air passageway, and wherein the apertures of said orifice plate place said culture media dish and the ambient air into fluid communication;

a removable cover for placement over said cassette and constructed so as to prevent air from entering into the cassette; and an air outlet port, said outlet port in fluid communication with said air passageway and adapted for connection to a suction pump.

* * * * *